United States Patent [19]

Miller et al.

[11] 3,950,236

[45] Apr. 13, 1976

[54] PRODUCTION OF ANGULAR ALKYLATED POLYCYCLIDES BY ELECTROCHEMICAL ANNELATION

[75] Inventors: Larry L. Miller; Frank R. Stermitz, both of Fort Collins, Colo.; J. Russell Falck, Albuquerque, N. Mex.

[73] Assignee: The United States of America as represented by the Secretary of Health, Education and Welfare, Washington, D.C.

[22] Filed: July 24, 1974

[21] Appl. No.: 491,610

[52] U.S. Cl. .................................................. 204/78
[51] Int. Cl.² ............................................ C25B 3/02
[58] Field of Search ..................................... 204/78

[56] References Cited
UNITED STATES PATENTS
2,960,452   11/1960   Slager et al. ......................... 204/78

*Primary Examiner*—R. L. Andrews
*Attorney, Agent, or Firm*—Holman & Stern

[57] ABSTRACT

A process of producing angular alicylated polycyclides by electrochemical annelation wherein a biphenyl compound containing an alkyl group is oxidized at the anode in an electrolyte to form the corresponding dieone.

6 Claims, No Drawings

PRODUCTION OF ANGULAR ALKYLATED POLYCYCLIDES BY ELECTROCHEMICAL ANNELATION

The subject invention is directed to a novel process for producing cyclic compounds having an angular alkyl group. In particular, the instant invention is directed to the anodic cyclization and rearrangement of alkoxy bibenzyl compounds to the corresponding phenanthrone compounds which are useful as precursors in the preparation of both steroids and terpenoids.

Annelelation reactions, notably those which result in an angular alkyl group, occupy a prominent position in numerous synthetic sequences. This is especially true in the total synthesis of complex molecules such as steroids and terpenoids wherein the presence of angular methyl groups impose stringent limitations on the number and scope of suitable methods of preparation.

The anodic coupling of dimethoxybenzene rings has recently been demonstrated to have utility and resulted in the production of a variety of morphinandienones.

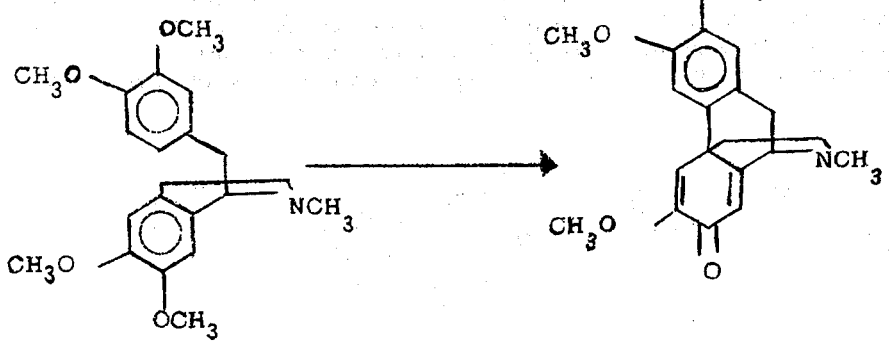
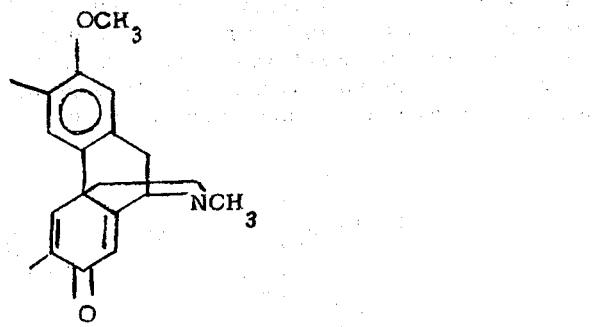

Moreover, the cyclization of an isochroman-3-one derivative has been reported by Sainsbury and Shinazi, with the cyclized product being isolated in about 50% yield in each case. It is also noted that cyclizations to produce tetramethoxydihydrophenanthrene cation radicals have also been reported by Parker et al., in all prior work. However, the preparation of such cyclic compounds wherein an angular alkyl group is present has created substantial difficulty. Moreover, the preparation of such compounds by electrochemical means has previously not been disclosed.

Therefore, it is an object of the subject invention to disclose a process for preparing a polycyclic compound having an angular alkyl group.

A further object of the subject invention is to prepare such polycyclic compounds by electrochemical means.

A still further object of the subject invention is to prepare phenanthrone compounds by electrochemical means, which compounds are useful in the preparation of steroid and terpenoid compounds.

These and other objects of the subject invention will become more evident from the following more detailed disclosure thereof.

As noted, the subject invention is directed to a process of producing angular alkylated polycyclides by electrochemical annelation. The reaction involved is not yet fully understood, but it is hypothesized that a very clean coupling reaction is produced which unexpectedly leads to the production of B C D rings by contraction of a dieone ring. Most importantly, the requisite alkyl group is in place. The data available are limited, but do allow a mechanistic hypothesis to be formulated as indicated in the following schematic drawing.

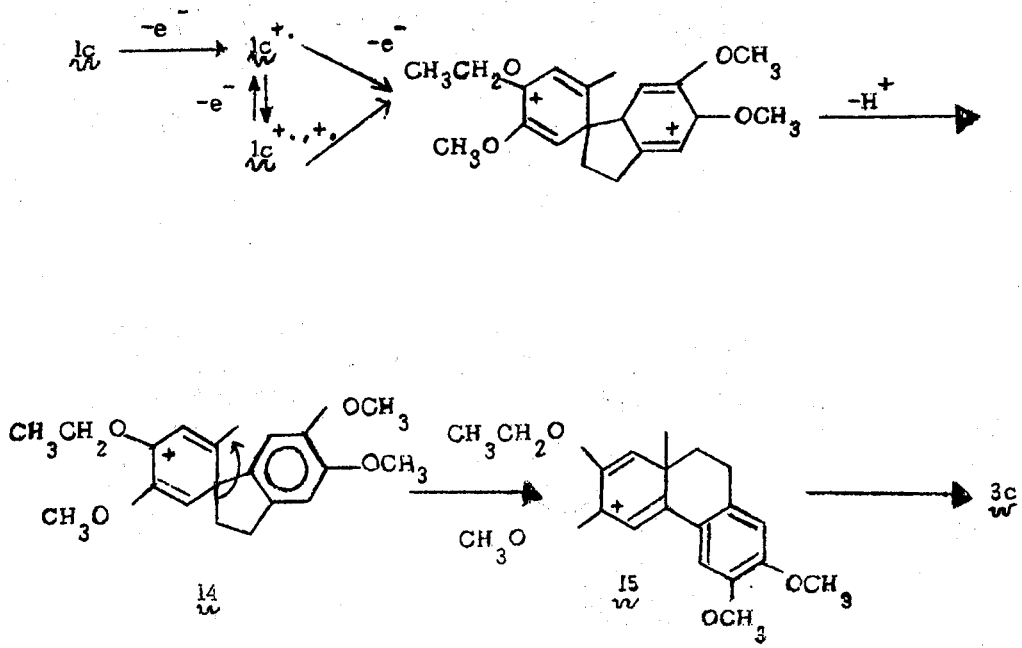

It is first noted that 2-methyl-4, 5-dimethoxybibenzyl gave a somewhat more stable cation radical and did not cylcize to an appreciable extent. This is rationalized by considering the unreactivity of phenyl compared to dialkoxyphenyl. If an initially formed cation radical attacked an unoxidized ring, it would resemble an electrophilic attack and the phenyl would be relatively inert. Alternatively, it may be that both rings are being oxidized to produce a bis-cation radical which gives radical coupling. Again phenyl would be unreactive due to its relatively high oxidation potential compared to the dialkoxy phenyl ring.

It is assumed, therefore, that for the subject biphenyls the coupling is the rapid follow-up reaction after an initial one or two electron transfer. After rearomatization of one ring by deprotonation, one can reach the cation 14 as noted in the schematic process shown. This cation by migration of the ethylene bridge gives a new, more stable cation 15, as noted above, which finally leads to the product by loss of methyl.

A major product in the anolyte is the red material, (λmax 416,503 nm) which is thought to be 15. The same species can be produced by independently treating 9,10-dihydro-10a-methyl-2-ethoxy 6,7-dimethoxy-3-(10aH) phenanthrone with trimethyloxonium fluoroborate. The hexadienone is thus methylated giving back the relatively stable cation. Since independently produced 15 is also hydrolyzed back to 9,10-dihydro-10a-methyl-2-ethoxy-6,7-dimethoxy-3-(10aH)phenanthrone, this strongly implies that demethylation is the last step in the reaction.

It is further noted that a five-membered ring instead of a six-membered ring is formed by coupling, according to the subject process. Since the O-methyl group is lost in the oxidation of 2-methyl-3',4',5'-trimethoxy-4-ethoxybibenzyl, it is indicated that the ring methyl does not migrate, but rather that the bridge undergoes a carbonium ion rearrangement of the type common to dienone-phenol rearrangements. The extra stability imparted by conjugation of the cation with the dimethoxybenzene ring in 15 clearly explains why this is the ultimate product.

According to the subject process, a bibenzyl compound having an appropriate alkyl group is oxidized electrochemically to produce the desired phenanthrone compound. The bibenzyl starting materials are prepared according to the following schematic wherein R represents a lower alkyl group having from 1 to about 5 carbon atoms; $R_1$, $R_2$, $R_3$, and $R_4$ represent either hydrogen, and/or a lower alkoxy group having from about 1 to about 5 carbon atoms. Preferably R is either a methyl or ethyl alkyl group and between $R_1$, $R_2$, $R_3$, and $R_4$. Two of same represent hydrogen when the other two represent either methoxy or ethoxy radicals.

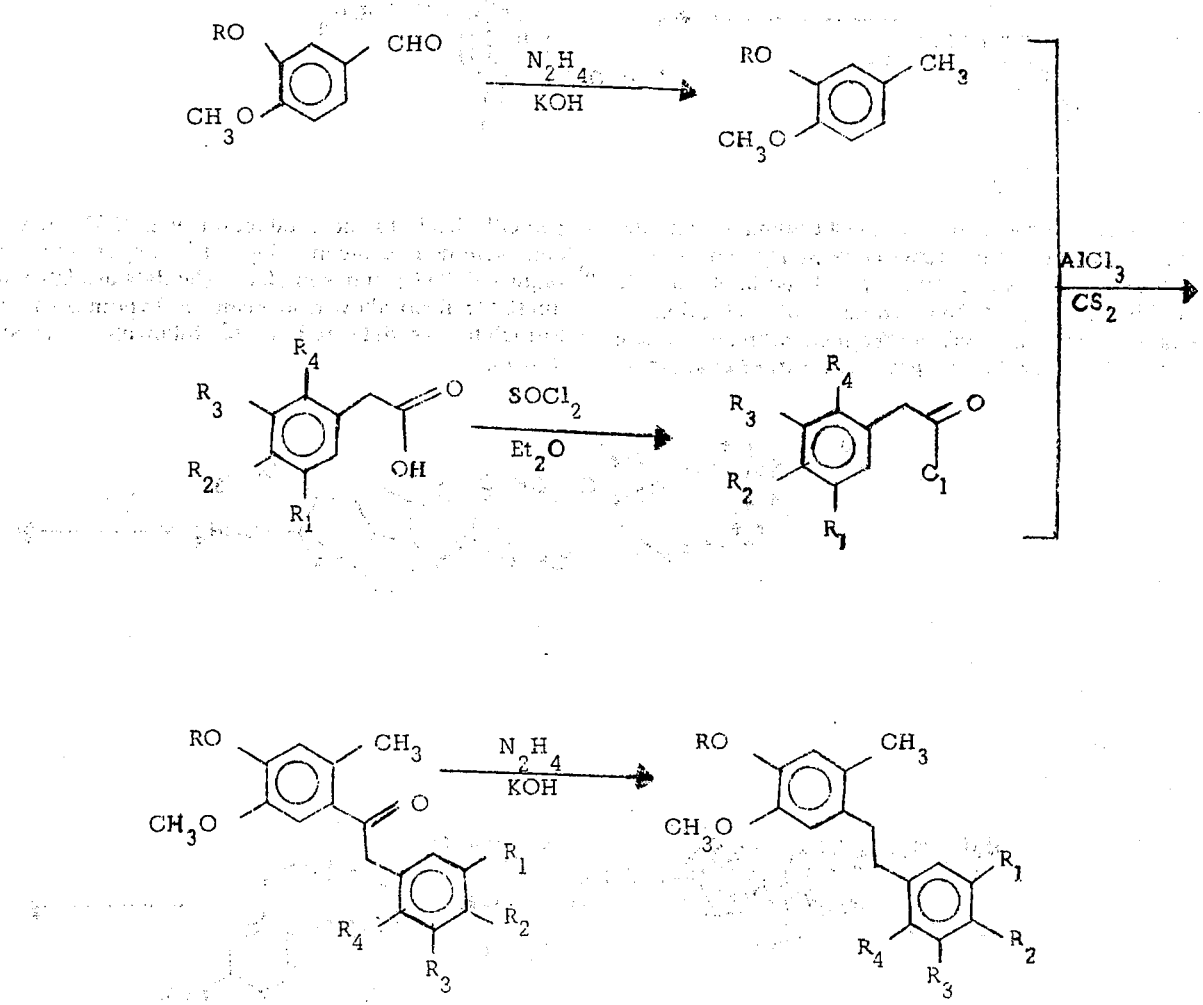

a: $R_1=R_4=H$, $R_2=R_3=OCH_3$, $R=CH_3$ b: $R_1=R_4=OCH_3$, $R_2=R_3=H$, $R=CH_3$ c: $R_1=R_4=H$, $R_2=R_3=OCH_3$, $R=CH_2CH_3$

In the preparation of 2-methyl-3',4,4', 5-tetramethoxybibenzyl, for example, 3,4-dimethoxytoluene was prepared from commercial veratraldehyde by the method of Bruce and Sutcliff, J. Chem. Soc., 3824 (1956). 3,4-Dimethoxyphenylacetyl chloride was prepared from commercial 3,4-dimethoxyphenylacetic acid and added to a stirred mixture of 3,4-dimethoxytoluene and aluminum chloride in carbon disulfide. After reaction, the previously unknown 4,5-dimethoxy-2-(3,4-dimethoxyphenylacetyl) toluene was isolated (based upon the 3,4-dimethoxyphenyl acetic acid) and converted by a modified Wolff-Kishner reaction to 2-methyl-3',4,4',5-tetramethoxybibenzyl.

2-Methyl-4,5-dimethoxybibenzyl was prepared by treating 4-methylveratrole to the Vilsmeier-Haack reaction to give 6-methylveratraldehyde in which the addition of excess benzylmagnesium chloride gave a quantitative yield of the a-hydroxybibenzyl. The alcohol was then converted to the corresponding chloride by treatment with thionyl chloride in ether and LAH reduction at room temperature resulting in 4,5-dimethoxy-2-methylbibenzyl. It is noted if that final reduction with LAH was performed at reflux, a white solid whose spectroscopy was consistent with a trans-stilbene structure was isolated in addition to 2-methyl-4,5-dimethoxybibenzyl, and hydrogenation over Adam's catalyst converted the white solid into 4,5-dimethoxy-2-methylbibenzyl in high yield.

The oxidation process of the subject invention is performed by oxidizing the above noted bibenzyl compounds in acetonitrile using lithium perchlorate as the background electrolyte in a three compartment cell described more fully in The Journal of the American Chemical Society, 93, 5941 (1971) and 94, 2651 (1973) P. 14(9).

The oxidation proceeds smoothly in either the presence or absence of solid sodium carbonate with no detectable change in yield. A red species is observed streaming from the surface of the anode, eventually turning the entire solution deep red, and at the end of the oxidation, and anolyte remained highly colored for days or until water was added, at which time it immediately turned pale yellow. The anolyte is then evaporated to near dryness, mixed with more water and extracted repeatedly with chloroform. The chloroform extracts yield a single product, which is essentially pure.

2-Methyl-3',4,4',5tetramethoxy bibenzyl can be oxidized at 0.90 V in acetonitrile at 0°C with lithium perchlorate as background electrolyte in the three compartment cell described previously. A red species is observed streaming from the surface of the anode, eventually turning the entire solution deep red, and at the end of the oxidation, the anolyte remained highly colored for days or until water was added, at which time it immediately turned pale yellow. The anolyte is then evaporated to near dryness, mixed with more water and extracted repreately with chloroform. The chloroform extracts yield a single product which is essentially pure, in 98% yield, mp 205°–206°. Its assignment to structure 9,10-dihydro-10a-methyl-2,6,7-trimethoxy-3-(10aH)-phenanthrone was based on its spectroscopic characteristics. The $C_{18}H_{20}O_4$ molecular formula was indicated by mass spectroscopy and verified by combustion analysis. The ir spectrum indicated the presence of a cross-conjugated 2-methoxycyclohexadienone system: $\nu_{max}$(Nujol mull) 1640, 1625, and 1605 cm$^{-1}$. This was corroborated by prominent ions at m/e 299 (m-1) and 257 (m-43) in the mass spectrum. Nuclear magnetic resonance spectroscopy ($\delta$ in $CDCl_3$) showed a tertiary methyl at 1.28 (s, 3H); one-half of an $A_2B_2$ system at 1.70–2.10 (m, 2H); the other half at 2.82–3.15 (m, 2H); two methoxy resonances at 3.78 (s, 3H, vinyl ether) and 3.95 (s, 6H, aromatic methoxys); two olefinic protons at 5.82 (s, 1H, a-proton of a, B-unsaturated ketone system) and 7.13 (s, 1H, a-proton of a, B-unsaturated ketone system); and two aromatic protons at 6.63 (s, 1H) and 6.70 (s, 1H).

It is known that signals corresponding to two protons on a substituted cyclohexadienone ring show appreciable spin-spin coupling when they are located in any of the following arrangements: (a) on adjacent carbon atoms, (b) on positions 2 and 6, (c) on positions 3 and 5. The absence of such coupling in the spectrum, assuming no skeletal rearrangement, indicated the partial structure 4.

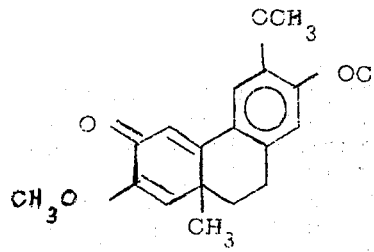

3a

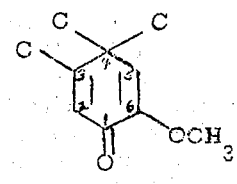

4

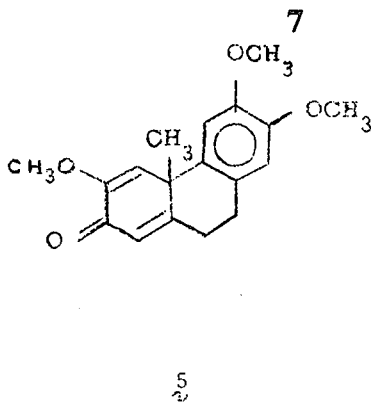

5

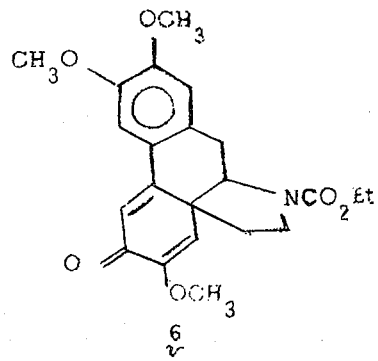

6

The appearance of the aromatic protons as two singlets indicated cyclization to the other ring occurred at the least hindered position, para to a methoxy group. Furthermore, the methyl group must be in the 4-position of the dienone ring since it is uncoupled and not shifted downfield as it would be if in an allylic position.

Two structures consistent with this data are 9,10-dihydro-10a-methyl-2,6,7-trimethoxy-3(10aH)-phenanthrone and 5. Compound 5 would be formed by simple cyclization and loss of the methoxy methyl in analogy with earlier examples. Neither the nmr nor uv-visible spectra are, however, in accord with this structure. Thus, the absorption spectrum shows several bands with a longest wave length $\lambda_{max}$=357 nm, and methoxycyclohexadienones do not have bands beyond 300 nm. On the other hand, B-arylcyclohexadienones should absorb at longer wave lengths. Indeed, the uv spectra of the product and model compound 6 are extremely similar throughout: 3a - $\lambda_{max}^{EtOH}$ (log $\epsilon$) 238 (4.33), 265 (4.35), 292 (4.26), 357 (4.41); 6 - $\lambda_{max}^{EtOH}$ (log $\epsilon$) 236 (4.08), 265 (4.07), 291 (3.79), 359 (3.99). The nmr spectrum of 5 should show allylic coupling between the vinyl proton at position 1 and the methylene protons at carbon 10 and, this coupling is seen in the model compound 7. On the other hand, no allylic coupling should be seen from 9,10-dihydro-10a-methyl-2,6,7-trimethoxy-3(10aH)-phenanthrone which is in agreement with the spectrum.

trimethoxy-4-ethoxybibenzyl produced only 9,10-dihydro-10a-methyl-2-ethoxy 6,7-dimethoxy-3 (10aH) phenanthrone, again in very high yield.

Thus an effective synthesis of dihydrophenanthrones has been disclosed. As previously noted, the reaction was originally conceived as a route to the A,B,C, rings of steroids. The unexpected coupling-rearrangement produced instead a ring system that could be used in the synthesis of the B,C,D rings by contraction of the dienone ring and most importantly, the requisite angular methyl is in place.

Preparative electrolysis of 4,5-dimethoxy-2-methylbibenzyl at 0.90 V and 0° (until coulometry indicated two Far/mole of current has been passed) gave a complex product mixture. Although a red colored species could be seen streaming from the anode surface, the reaction mixture quickly turned dark brown and remained so throughout the oxidation and work-up procedure. The product mixture was chromatographed on silica gel to give unreacted starting material, 6-methylveratraldehyde 9, 6-methylveratryl alcohol 10, benzylacetamide 11, and 2-methyl-4,5-dimethoxy-a-hydroxybibenzyl 12. These products were identified by spectral comparison with authentic samples. In addition, a small amount of yellow oil was isolated and assigned structure 13, based on its spectral characteristics. The ir spectrum indicated an aryl ketone: $\lambda_{max}$ (neat) 1675 cm$^{-1}$. Nmr showed an aryl methyl resonance at 2.42 (s, 3H), one methoxy resonance at 3.72

Electrolysis of 2-methyl-2',4,5',5'-tetramethoxybibenzyl at 0.86 V at 0° gave only one product, mp 184°–185.5° in 88% yield. As above, a persistent red species was generated which readily discharged to pale yellow when water was added. With a similar foundation as above, the product was assigned the structure, 9,10-dihydro-10a-methyl-2,5,8-trimethoxy-3(10aH),-phenanthrone. The oxidation of 2-methyl-3',4',5-

(s, 6H), a singlet at 4.15(2H), in the correct region for a methylene between a phenyl and a carbonyl, and three aromatic singlets at 6.65 (1H), 7.21 (5H), and 7.40 (1H). Structure 13 was confirmed by reduction of the electrolysis product by sodium borohydride in methanol to give a yellow oil whose infrared spectrum was superimposable on that of 2-methyl-4,5-dimethoxy-a-hydroxybibenzyl,12.

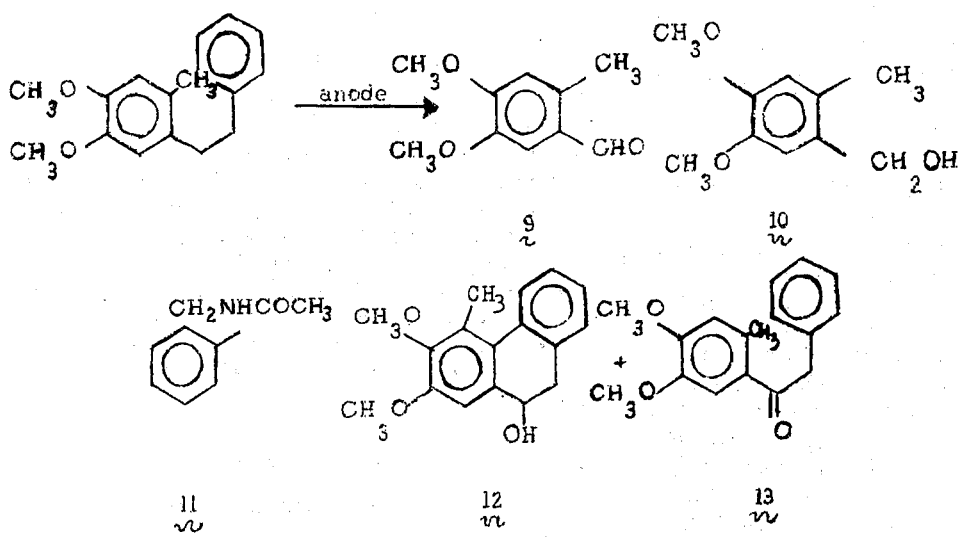

Further testing of the subject process was performed with voltammograms which were recorded using an acetonitrile-lithium perchlorate electrlyte solution. A two compartment cell was employed at room temperature under a nitrogen atmosphere in which the Ag/AgNO₃ reference electrode was separated from the platinum anode and the cathode by a glass frit. Either lithium perchlorate or tetramethylammonium tetrafluoroborate were used to maintain an approximate 0.1N solution of electrolyte. Model compound 4,5-dimethylveratrole showed a quasi-reversible couple centered at 0.85 V. The peak separation ($Ep_a - Ep_c$) was 75 mv at a scan rate of 500 m V/sec, thus demonstrating that the cation radical has a lifetime greater than 1 sec. Similar behavior was noted for 4,5-dimethoxy-2-methylbibenzyl where $Ep_a - Ep_c = 80$ mv. 2-Methyl-2',4,4',5-tetramethoxybibenzyl and 2-methyl-2',4,5,5'-tetramethoxybibenzyl in contrast did not show any cathodic peak on the reverse sweep demonstrating that these cation radicals are unstable, on this time scale. $Ep_a$ values are reported in Table I. The similarlity of the first peak potentials for 2-methyl-3',4,4',5-tetramethoxybibenzyl, 2-methyl-2',4,5',5'-tetramethoxybibenzyl, 4,5-dimethoxy-2-methylbibenzyl and 4,5-dimethylveratrole suggests that initial transfer involves the tetrasubstituted ring. The $Ep_a$ of 4-methylveratrole is however, close enough so that this is not a firm conclusion and indeed, one electron oxidation of both rings may precede coupling. Comparison of the $Ep_a$ for the anodic product 9,10-dihydro-10a-methyl-2,6,7-trimethoxy-3 (10aH)-phenantrone and 2-methyl-3',4,4',5-tetramethoxybibenzyl demonstrates that the dienone oxidizes somewhat more difficulty than the bibenzyl and hence overoxidation can be avoided with controlled potentials.

Table 1

| Peak potentials from cyclic voltammetry[a] | |
|---|---|
| Substrate | $Ep_a$ (V) |
| 2-methyl-4,5-dimethoxybibenzyl | 0.87, 1.44, and 1.87 |
| 2-methyl-3',4',4,5-tetramethoxybibenzyl | 0.90, 1.17, 1.37, and 1.65 |
| 2-methyl-2',4,5',5-tetramethoxybibenzyl | 0.90, 1.00, and 1.40 |
| 4,5-dimethylveratrole | 0.90, 1.57, and 1.80 |
| 4-methylveratrole | 0.97, 1.12, 1.57, and 2.20 |
| 9,10-dihydro-10a-methyl-2,6,7-trimethoxy-3(10aH)-phenanthrone | 1.10, 1.3, 1.8 |

[a]CH₃CN-LiClO₄ solution, Ag/0.1 N AgNO₃ reference scan rate 500 mv/sec over 0–2 V range.

EXAMPLE I

3,4-Dimethoxytoluene

A mixture of veratraldehyde (91.5g), KOH (100 g), 95% hydrazine (75 ml) and ethylene glycol (700 ml) was heated at reflux until the KOH disappeared (30 min). The hydrazone then separated as a yellow solid and mild foaming occurred. The heating was continued at reflux causing evolution of N₂ and vigorous frothing. After 3 hr., the solution was cooled, poured into 1.5 l of cold water and the resulting oil was extracted into ether. The combined extracts were washed with water, dried and evaporated to yield a yellow oil which was distilled to give 65.7 g of the product, 3,4-dimethoxy toluene as a colorless oil (bp 68°–72°at 0.05 mm).

EXAMPLE II

4,5-Dimethoxy-2-(3,4-dimethoxyphenylacetyl) toluene

To a stirred solution of 35.6 g (0.24 mole) of 3,4-dimethoxytoluene and 14.6 g (0.11 mole) AlCl₃ in 200 ml CS₂ there was added dropwise over the course of 1 hr. 0.1 mole 3,4-dimethoxyphenylacetyl chloride (freshly prepared from 3,4-dimethoxyphenylacetic acid). The mixture was stirred overnight at 25°, poured into ice, and the resulting oil extracted into benzene. The extracts were dried and evaporated to yield a black viscous oil from which excess dimethoxytoluene was distilled in vacuo. After the pot residue had cooled, alcohol was added and the mixture was allowed to stand 24 hr at 0°. This allowed isolation of essentially pure ketone 4,5-dimethoxy-2-(3,4-dimethoxyphenylacetyl) toluene as a brown powder (25.4 g or 80% yield based upon the acid chloride). An analytical sample was recrystallized from EtOH-EtOAc to yield 4,5-dimethoxy-2-(3,4-dimethoxyphenylacetyl) toluene as white needles, mp 115°. Nmr (δ): 2.52 (s, 3H), 3.82 (s, 6H), 3.85 (s, 3H), 3.88 (s, 3H), 4.15 (s, 2H), 6.68 (s, 1H), 6.77 (s, 3H), 7.30 (s, 1H). Anal. Calcd for C₁₉H₂₂O₅: C, 69.07; H, 6.71. Found: C, 68.84; H, 6.93.

EXAMPLE III

2-Methyl-3',4,4',5-tetramethoxybibenzyl

Reaction of 8.0 of 4,5-dimethoxy-2(3,4-dimethoxyphenylacetyl) toluene and 10 g KOH in a solution of 6.5 ml 95% hydrazine in 84 ml triethylene glycol according to the procedures of Example II gave a yellow oil which was crystallized from alcohol to give 6.4 g (82%) of 2-methyl-3',4,4',5-tetramethoxybibenzyl as a white powder, mp 101.5°–102.5°. Nmr (δ): 2.20 (s, 3H), 2.82 (s, 4H), 3.80 (s, 3H), 3.84 (s, 9H), 6.58–6.80 (m, 5H); mass spectrum: m/e (rel intensity) 316(5), 165(100), 151 (15). Anal. Calcd. for $C_{19}H_{24}O_4$: C, 72.13; H, 7.65. Found: C, 72.15; H, 7.69.

EXAMPLE IV 9,10-Dihydro-10a-methyl-2,6,7-trimethoxy-3(10aH)-phenanthrone

Oxidation of 316 mg of 2-methyl-3',4,4'5-tetramethoxybibenzyl at 0.90 V at 0° gave a dark brown solid which was recrystallized from alcohol and combined with crystals from the mother liquors to yield 295 mg (98%) of 9,10-dihydro-10a-methyl-2,6,7-trimethoxy-3(10aH)-phenantrone, as buff colored needles, mp 204°–205°. An analytical sample was recrystallized from ethanol to give white needles, mp 205°–206°. Nmr (δ): 1.28 (s, 3H), 1.70–2.10 (m, 2H), 2.82–3.15 (m, 2H), 3.78 (s, 3H), 3.95 (s, 6H), 5.82 (s, 1H), 6.63 (s, 1H) 6.70 (s, 1H); ir: $\lambda_{max}$ (Nujol) 1640, 1625, 1605, 1575 cm$^{-1}$; mass spectrum: m/e (rel intensity) 300 (17), 299 (63), 257 (100); uv (EtOH): $\lambda_{max}$ (log ε) 2.2 (4.74), 238 (4.33), 265 (4.35), 292 (4.26), 357 (4.41). Anal. Calcd. for $C_{18}H_{20}O_4$: C, 71.98; H, 6.71. Found: C, 71.96; H, 6.65.

EXAMPLE V 4,5-Dimethoxy-2-(2,5-dimethoxyphenylacetyl)toluene

Reaction of 74.1 g of 3,4-dimethoxytoluene and 18.6 g $AlCl_3$ in 300ml $CS_2$ with 25 g of freshly-prepared 2,5-dimethoxyphenylacetyl chloride gave 30.5 g of 2b as a white powder, mp 76°–77° from ethanol. Nmr (δ): 2.53 (s, 3H), 3.78 (s, 6H), 3.90 (s, 3H), 3.93 (s, 3H), 4.16 (s, 2H), 6.70–6.88 (m, 4H), 7.40 (s, 1H). Anal. Calcd. for $C_{19}H_{22}O_5$: C, 69.07; H, 6.71. Found: C, 68.95; H, 6.52.

EXAMPLE VI 2-methyl-2',4,5',5'-tetramethoxybibenzyl

Reaction of 16.5 of 4,5-dimethoxy-2-(2,5-dimethylphenylacetyl)toluene in 200 ml diethylene glycol with 20 g KOH and 12 ml 95% hydrazine according to the procedure of Example III yielded a yellow oil which crystallized from alcohol to give 14.3 g (88%) of 2-methyl-2',4,5',5'-tetramethoxybibenzyl as a light brown powder, mp 69°–70°. An analytical sample was prepared by sublimation to yield a white powder, mp 71°–72°. Nmr: (δ): 2.25 (s, 3H), 2.83 (s, 4H), 3.66 (s, 3H), 3.70 (s, 3H), 3.75 (2, 3H), 3.80 (s, 3H), 6.62–6.80 (m, 5H). Anal. Calcd. for $C_{19}H_{24}O_4$: C, 72.13; H, 7.65. Found: C, 71.99; H, 7.73.

EXAMPLE VII 9,10-Dihydro-10a-methyl-2,5,8-trimethoxy-3(10aH)-phenanthrone 343 mg of 2-methyl-2',4,5',5'-tetramethoxybibenzyl was oxidized according to the procedure of Example IV and at 0.86 V gave a dark colored solid. Crystallization of the solid and work-up of the mother liquors in the same way gave 288 mg (88%) of 9,10-dihydro-10a-methyl-2,5,8-trimethoxy-3(10aH) phenanthrone, m.p. 184°–185.5°, Nmr (δ): 1.26 (s, 3H), 1.75–2.08 (m, 2H), 2.68–3.02 (m, 2H), 3.74 (s, 3H), 3.78 (s, 3H), 3.81 (s, 3H), 5.82 (s, 1H), 6.77 (s, 2H), 7.23 (s, 1H) ir (Nujol): 1650, 1630, 1600, and 1580 cm$^{-1}$; uv (EtOH): $\lambda_{max}$ (logε) 213 (4.55), 235sh (3.99), 273 (4.22), 286 (4.27), 315sh (4.03), 357 ) 3.85). Anal. Calcd. for $C_{18}H_{20}O_4$: C, 71.98; H, 6.71. Found: C, 71.63; H, 6.63.

EXAMPLE VIII

3-Ethoxy-4-methoxybenzaldehyde

To a solution of 100 g of 3-hydroxy-4-methoxybenzaldehyde in 200 ml ethanol was added to solution of 44 g KOH in 44 ml $H_2O$. The mixture dissolved upon heating to reflux and 56 ml ethyl bromide was then added slowly. A yellow solid began to precipitate after 15 min and heating of the mixture at reflux was continued overnight. Excess ethyl bromide and solvent were removed in vacuo and the residue was distributed between water and $CHCl_3$. The $CHCl_3$ layer was dried and evaporated to give a pale yellow oil which crystallized from ethanol to give 112 g (93%) of 3-ethoxy-4-methoxybenzaldehyde, mp 49.5°–50.5°(Lit.[12] mp 50°–51°).

EXAMPLE IX

3-Ethoxy-4-methoxytoluene

3-Ethoxy-4-methoxybenzaldehyde (112g) was treated with 120 g of KOH, 87 ml 95% hydrazine and 840 ml diethylene glycol according to the procedure of Example I to yield a yellow oil. Distillation yielded 94 g (91%), bp 64°–69° at 1 mm (Lit.[13] bp 120° at 30 mm).

EXAMPLE X

5-Ethoxy-4-methoxy-2-(3,4-dimethoxyacetyl)toluene

3-Ethoxy-4-methoxytoluene (94 g) was reacted with 74.8 g of $AlCl_3$ and 29.4 g of 3,4-dimethoxyphenylacetyl chloride in 300 ml $CS_2$ according to the procedure of Example II. A total of 40.0 g (87%) of 2c was obtained after crystallization from ethanol, mp 106°–107°. Nmr (δ): 1.47 (t, 3H), j=7 cps), 2.52 (s, 3H), 3.88 (s, 9H), 4.15 (q, 2H), J = 7 cps), 4.16 (s, 2H), 6.75 (s, 1H), 6.80 (s, 3H), 7.35 (s, 1H). Anal. Calcd. for $C_{20}H_{24}O_5$: C, 69.75; H, 7.02. Found: C, 69.42, H, 7.23.

EXAMPLE XI

2-Methyl-3',4',5-trimethoxy-4-ethoxybibenzyl

According to the procedure of Example III, 35.1 g of the ketone was reacted with 20 g KOH, 14.5 ml 95% hydrazine and 140 ml diethylene glycol to give 25 g of 2-methyl-3',4",5-trimethoxy-4-ethoxybibenzyl as a colorless oil (bp 175° at 0.1 mm). The oil could be obtained crystalline from ethanol with care: mp 38.40°. Nmr (δ): 1.42 (t, 3H, J = 7 cps), 2.19 (s, 3H), 2.79 (s, 4H), 3.76 (s, 3H), 3.79 (s, 3H), 3.81 (s, 3H), 4.07 (q, 2H, J = 7 cps), 6.58–6.79 (m, 5H). Anal. Calcd. for $C_{20}H_{26}O_4$: C, 72.70, H, 7.93. Found: C, 72.68, H. 8.16.

EXAMPLE XII 9,10-Dihydro-10a-methyl-2-ethoxy-6,7-dimethoxy-3-(10aH)- phenanthrone 360 mg of 2-methyl-3',4',5-trimethoxy-4-ethoxybibenzyl was oxidized according to the procedure of Example IV and at 0.80 V yielded 340 mg of black oil after the usual work-up. This oil was recrystallized from ethanol to yield 302 mg (86%) of a 2-methyl-3',4,5-trimethoxy-4-ethoxybibenzyl, mp 178°–179.5°. Nmr (δ): 1.21 (s, 3H), 1.45 (t, 3H, J = 7 cps), 1.95 (m, 2H), 2.95 (m, 2H), 3.80 (q, 2H, J = 7 cps), 3.90 (s, 9H), 5.79 (s, 1H), 6.60 (s, 1H), 6.68 (s, 1H), 7.08 (s, 1H); uv (ethanol: $\lambda_{max}$ 238 (log ε= 3.99), 264 (logε= 4.01), 289 (logε= 3.93), 353(logε 4.11). Anal. Calcd. for $C_{19}H_{22}O_4$: C, 72.60; H, 7.01. Found: C, 71.8, H, 6.9.

EXAMPLE XIII

6-Methylveratraldehyde

Freshly distilled POCL$_3$ (50.6 ml) was added dropwise during 30 min to a stirred mixture of 4-methylveratrole (65.7 g) and DMF (30 g) freshly distilled after standing two days over CuSO$_4$. Heating overnight on a steam bath under reflux gave a deep brown, viscous solution which when cooled was admixed with 600 ml water. Addition of excess 10% NaOH solution separated out a yellow oil which was extracted with benzene. The combined extracts were washed with water, dried, and evaporated to give a viscous yellow oil. Crystallization from alcohol gave 3.4 g of the aldehyde as a white powder, mp 74°–75°(Lit. 74°). Nmr ($\delta$): 2.58 (s, 3H), 3.90 (s, 3H), 3.95 (s, 3H), 6.68 (s, 1H), 7.30 (s, 1H), 10.20 (s, 1H).

EXAMPLE XIV

4,5-Dimethylveratrole 1.80 g of 6-methylveratraldehyde was treated with 2 g KOH, 1.4 ml 95% hydrazine, and 20 ml diethylene glycol in the manner described in the preparation of 3,4-dimethoxytoluene to give a quantitative yield of 4,5-dimethylveratrole as a cream colored solid. An analytical sample was sublimed (60°/0.05 mm Hg) to give a white powder, mp 41°–42°(Lit. 42.5°). Nmr ($\delta$): 2.19 (s, 6H), 3.85 (s, 6H), 6.66 (s, 2H).

EXAMPLE XV a-Hydroxy-4,5-dimethoxy-2-methylbibenzyl

To 10 g of 6-methylveratraldehyde under a nitrogen atmosphere in 75 ml dry THF was added dropwise 1.5 equivalents benzylmagnesium chloride in 20 ml dry THF. After stirring overnight at room temperature, 20 ml water was added. The residue remaining after most of the THF had been distilled off was added to an additional 100 ml water and extracted with ether to give a yellow oil. Distillation under reduced pressure gave bibenzyl resulting from coupling of the Grignard reagent and a quantitative yield of the adduct 12 as a colorless viscous oil, bp 170°–175°(0.05 mm Hg). Nmr ($\delta$): 2.08 (s, 3H), 2.88 (distorted doublet, J - 6 cps, integration for 3H suggests coincidence with the alcohol proton), 3.75 (s, 6H), 4.96 (t, J = 6 cps, 1H), 6.52 (s, 1H), 7.00 (s, 1H), 7.15 (s, 5H),. Anal. Calcd. for C$_{17}$H$_{20}$O$_3$: C, 74.97; H, 7.40. Found: C, 75.38; H, 7.43.

EXAMPLE XVI

4,5-Dimethoxy-2-methylbibenzyl (1d)

To a solution of 10 g 12 in 200 ml dry ether and 50 ml dry THF containing 0.5 ml pyridine was added portionwise a solution of 10 ml thionyl chloride in 20 ml dry ether during 30 min with stirring. After an additional 20 min. at room temperature, the reaction was cautiously quenched with cold water. Separation and evaporation of the ethereal layer gave 10 g of product as a pale yellow, mobile oil. The ir showed no OH absorption. A solution of 1g of this product in 5ml dry ether was added dropwise to a stirred solution of 300 mg LAH in 50 ml dry ether at room temperature. After stirring over night, the reaction was cautiously quenched with wet ether. The separated aluminate was filtered and washed generously with ether. The organic filtrate was washed with water, dried and evaporated to give a mobile yellow oil. Distillation (110°–115°/0.05 mm Hg) gave 680 mg colorless oil. Nmr ($\delta$): 2.20 (s, 3H), 2.80 (s, 4H0,. 3.75 (s, 3H), 3.80 (s, 3H), 6.53 (s, 1H), 6.60 (s, 1H), 7.17 (s, 5H), Mass spectrum: m/e 256 (13%), 165 (100%), and 91 (39%). Anal. Calcd. for C$_{17}$H$_{20}$O$_2$: C, 79.65; H, 7.86. Found: C, 79.41; H, 8.11.

The embodiments of the invention in which an exclusive property or privilege is claimed are defined as follows:

1. An electrochemical process for producing angular alkylated polycyclides comprising oxidizing a lower alkyl substituted alkoxy bibenzyl compound in an acetonitrile electrolyte in the presence of lithium perchlorate background electrolyte at a voltage of from 0.80 V to 2.25 volts.

2. The process of claim 1 wherein a three-compartment cell with the anode, cathode, and reference electrode solutions separated by glass frits is utilized.

3. The process of claim 1 wherein the bibenzyl compound is 2-methyl-3',4,4',5-tetramethoxybibenzyl.

4. The process of claim 1 wherein the bibenzyl compound is 2-methyl-2',4,5',5'-tetramethoxybibenzyl.

5. The process of claim 1 wherein the bibenzyl compound is 2-methyl-3',4',5-trimethoxy-4-ethoxybibenzyl.

6. The process of claim 1 wherein the bibenzyl compound is 4,5-dimethoxy-2-methylbibenzyl.

* * * * *